United States Patent
Su et al.

(10) Patent No.: US 7,973,036 B2
(45) Date of Patent: Jul. 5, 2011

(54) 2-METHYL-5-IMINO-BENZO[D][1 ,3]OXAZIN[5-B]PYRAZOLE COMPOUND, PREPARATION AND USE THEREOF

(75) Inventors: Guoqiang Su, Jiangsu (CN); Yicai Gao, Shandong (CN); Guirong Sun, Shandong (CN); Liming Wu, Shandong (CN); Yu Ren, Jiangsu (CN)

(73) Assignees: Qingdao Huanghai Pharmaceutical Co., Ltd, Keyuan, Laoshan, Qingdao, Shandong (CN); Nanjing Zhongrui Medicine Co., Ltd., Nanjing, Jiangsu (CN)

( * ) Notice: Subject to any disclaimer, the term of this patent is extended or adjusted under 35 U.S.C. 154(b) by 0 days.

(21) Appl. No.: 13/054,674

(22) PCT Filed: Mar. 20, 2009

(86) PCT No.: PCT/CN2009/070905
§ 371 (c)(1),
(2), (4) Date: Jan. 18, 2011

(87) PCT Pub. No.: WO2010/006521
PCT Pub. Date: Jan. 21, 2010

(65) Prior Publication Data
US 2011/0118247 A1    May 19, 2011

(30) Foreign Application Priority Data
Jul. 18, 2008 (CN) ............... 2008 1 0022314

(51) Int. Cl.
*C07D 498/04* (2006.01)
*A61K 31/5386* (2006.01)

(52) U.S. Cl. .................. 514/230.2; 544/95

(58) Field of Classification Search ............ 544/95; 514/230.2
See application file for complete search history.

(56) References Cited

U.S. PATENT DOCUMENTS
7,745,432 B2 * 6/2010 Tahri et al. ........... 514/230.2

FOREIGN PATENT DOCUMENTS
WO PCT/CN2009/070905    7/2009
* cited by examiner

*Primary Examiner* — Kahsay T Habte
(74) *Attorney, Agent, or Firm* — Global IP Services; Tianhua Gu (57) ABSTRACT

The present invention disclosed compound 2-methyl-5-imino-benzo[d][1,3]oxazin[5-b]pyrazole and preparation method and uses thereof. The compound 2-methyl-5-imino-benzo[d][1,3]oxazin[5-b]pyrazole of the present invention has the following structure of formula (II), wherein the compound or pharmaceutically acceptable salts thereof can be used for preparing the drugs for treatment or prevention of cardiovascular diseases.

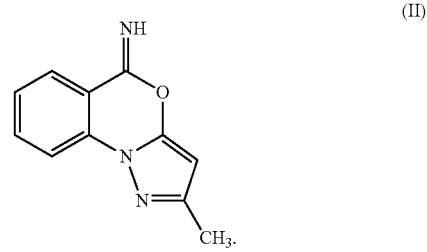

(II)

5 Claims, 3 Drawing Sheets

2-METHYL-5-IMINO-BENZO[D][1,3]OXAZIN[5-B]PYRAZOLE COMPOUND, PREPARATION AND USE THEREOF

CROSS REFERENCE TO RELATED PATENT APPLICATION

The present application is the US national stage of PCT/CN2009/070905 filed on Mar. 20, 2009, which claims the priority of the Chinese patent application No. 200810022314.6 filed on Jul. 18, 2008, which application is incorporated herein by reference.

FIELD OF THE INVENTION

The present invention belongs to the field of pharmaceutical chemistry, which particularly relates to 2-methyl-5-imino-benzo[d][1,3]Oxazin[5-b]pyrazole compound and preparation method and uses thereof.

BACKGROUND OF THE INVENTION

Thrombosis is the pathological basis of cerebrovascular diseases with high disability rate and lethality rate, such as stroke, which is a disease process involving various factors, like blood vessels, blood, blood flow. Thrombosis is related to coagulation system, endothelial cell function and dysfunction of cell adhesion, etc. Antithrombotic drugs include anticoagulants, antiplatelet drugs and endothelial cell-targeted drugs. Commonly used clinical anti-platelet drugs include aspirin, ticlopidine and clopidogrel; platelet GP II b/11Ia receptor antagonists include monoclonal antibody like abciximab, synthetic peptide receptor antagonist like eptifibatide, non-peptide receptor antagonists like tirofiban and non-peptide mimetics like lanifiban.

After stroke attacked, the occlusive artery unblocked in a short time may restore the brain function, but continuous ischemia over a period of time will result in irreversible brain cell damage. The area around the irreversible injured ischemic center is available penumbra. Even the blood supply is restored in a certain time, part of brain cells still had delayed neuronal death, which will cause various related factors, such as the release of excitatory amino acids, nerve cells calcium influx and free radicals etc, especially production of free radicals is considered to be one of main factors causing brain dysfunction. In ischemic state, hyperthyroidism of arachidonic acid metabolism can lead to the increase of free radical production, and peroxidation of unsaturated fatty acids forming cell membrane phospholipids will cause cell membrane damage and increase the dysfunction of brain cells.

Cranial nerve protection is an important part of stroke therapy. Brain protective agent edaravone was firstly recommended according to evidences of evidence-based medicine in latest Japanese stroke treatment guidelines, which injected new life for the treatment of stroke. In the treatment of acute cerebral infarction, edaravone with cerebral protecting action was recommended. Clinical studies showed that edaravone was effective for improving the prognosis of patients with acute cerebral infarction (occurred within 72 hours), especially more significant within 24 hours of the onset.

Edaravone

SUMMARY OF THE INVENTION

An objective of the present invention is to provide a compound 2-methyl-5-imino-benzo[d][1,3]oxazin[5-b]pyrazole or pharmaceutically acceptable salts thereof with medicinal value.

Another objective of the present invention is to provide a method for preparing the above compound.

Further objective of the present invention is to provide the use of the compound or pharmaceutically acceptable salts thereof.

The objectives of the present invention can be achieved through the following measures:

The first aspect of the invention is to provide a compound of formula (II), 2-methyl-5-imino-benzo[d][1,3]oxazin[5-b]pyrazole (II)

or pharmaceutically acceptable salts thereof.

The pharmaceutically acceptable salts referred to herein are general salts produced by the above compound and pharmaceutically used general acid or base, with no other side effects and increased chemical properties (like water-solubility, etc.), in which the acid or base is often selected from hydrochloric acid, hydrobromic acid, sulfuric acid, nitric acid, phosphoric acid, succinic acid, maleic acid, fumaric acid, acetic acid, citric acid, tartaric acid, benzoic acid, naphthalene sulfonic acid, hydrogen sodium, sodium carbonate, sodium bicarbonate or potassium hydroxide, etc.

The second aspect of the invention is to provide a method for preparing compound of formula II: comprising steps of (1) reacting compound M with an acetyl acetate in the existence of a base to give compound N; and (2) making compound N ring-closed in hydrogen chloride gas. The reaction equation of which is as follows:

formula II

In the first step reaction, the reaction solvent is an alcohol, such as ethanol or methano; the base is a sodium alkoxide, such as sodium methoxide, sodium ethoxide, etc; and the reaction temperature is from 40 to 80° C. In the second step reaction, the solvent is dichloromethane or THF, and the reaction temperature is from 20 to 40° C.

The compound of the present invention or pharmaceutically acceptable salts thereof can be used in the pharmaceutical field, such as drugs for treatment or prevention of cardio-cerebrovascular diseases. It has be shown in pharmacodynamic experiments that the compound of the present invention, 2-methyl-5-imino-benzo[d][1,3]oxazin[5-b]pyrazole (hereinafter referred to as TR), can significantly improve the neurological defect symptoms of cerebral ischemia-reperfusion animals in a dose-dependent manner, decrease the cerebral infarction area, reduce the severity of brain injury, relieve the brain edema and inhibit the lipid peroxidation of injured brain tissue with onset dose of 3 mg/kg.

DETAILED DESCRIPTION OF THE INVENTION

Example I

Preparation of 2-methyl-5-imino-benzo[d][1,3]oxazin[5-b]pyrazole (compound II)

Preparation of 2-hydrazino benzonitrile hydrochloride 600 ml of concentrated hydrochloric acid, 500 ml of crushed ice and 59 g (0.5 mol) of 2-aminobenzonitrile were added into a 2000 ml three-neck flask and stirred until completely dissolved. The mixture was placed in ice salt bath till −7~−3° C., and dropped with sodium nitrite solution (34.5 g (0.5 mol) sodium nitrate dissolved in 150 ml water). After dropping completed, the mixture was stirred for 10 min to give orange yellow clear solution for using.

350 g of stannous chloride and 1000 ml of concentrated hydrochloric acid were added into a 5000 ml three-neck flask and stirred until completely dissolved. The mixture was placed in ice salt bath till −5° C., and dropped with the above diazonium salt solution to obtain white precipitate. After dropping completed, the mixture was continuously stirred for 2 hours and filtered. The filter cake was washed with a large number of NaCl saturated solution, and then washed with cold 15% hydrochloric acid and dried to obtain 36 g of 2-hydrazino benzonitrile hydrochloride.

Preparation of 1-(2-cyanophenyl)-3-methylpyrazol-5-one 8.5 g (0.05 mol) of 2-hydrazino benzonitrile hydrochloride, 6 g (0.05 mol) of methyl acetoacetate and 100 ml of methanol were added into a 250 ml reaction flask, and then 50% methanol sodium solution (5.5 g (0.051 mol) sodium methoxide dissolved in 50 ml methanol) was added under stirring. After stirring for 10 min, the mixture was heated and refluxed for 6 h, and immediately filtered. The solid was washed with 20 ml of methanol. The methanol was recovered until the remained volume was 50 ml. 200 ml of ice water was poured with stirring to give the solid. The solid was filtered and washed with water to give 7 g of light yellow solid.

Preparation of 2-methyl-5-imino-benzo[d][1,3]oxazin[5-b]pyrazole (compound II)

Dry hydrogen chloride gas was pumped into 20 g (0.1 mol) of 1-(2-cyanophenyl)-3-methylpyrazol-5-one and 200 ml of anhydrous tetrahydrofuran with stirring till the saturation was reached. The mixture was stirred at room temperature overnight, and concentrated to dry under vacuum. Then 100 ml of anhydrous tetrahydrofuran and 10 g of anhydrous sodium acetate were added and stirred at room temperature for 1 h followed by filtration. The tetrahydrofuran was concentrated under vacuum. Resulting solution was recrystallized with ethyl acetate to give 13 g of off-white crystal.

M/Z [M+1]+, 200; [M+Na]+, 222.

$^1$HNMR: δ13.2693 ppm (NH); 8.0219 ppm (1H, d); 7.611 ppm (1H, d); 7.459 ppm (1H, s); 7.0941 ppm (1H, s); 5.9555 ppm (1H, s); 2.467 ppm (3H, s).

$^{13}$CNMR: δ154.5172 ppm; 154.2973 ppm; 142.589 ppm; 140.0084 ppm; 136.0494 ppm; 124.4878 ppm; 123.4394 ppm; 113.0434 ppm; 109.6637 ppm; 102.6622 ppm; 19.7732 ppm.

Anti-DPPH Free Radical Test 2,2-diphenyl-1-picrylhydrazyl (DPPH) free radical spectrophotometry is a simple method for screening antioxidants, the principle of which is using the characteristic absorption peak of DPPH solution at 517 nm. When free radical scavengers existed, single electron pairing between free radical scavenger and DPPH allowed the absorption of DPPH disappeared, and its decoloring degree and accepted electron number present as quantitative relation, and the antioxidant activity of samples can be evaluated through the amount of cleared DPPH, so the spectrophotometry can be used for quantitative analysis.

DPPH Standard Curve

DPPH was accurately weighed and placed in a volumetric flask, and diluted to 100 ml with 95% ethanol. The absorbance (A) of DPPH was measured at 517 nm.

TABLE 1

Absorption value of DPPH solution of different concentrations

| | DPPH concentration (mg/100 ml) | | | | |
|---|---|---|---|---|---|
| | 5.360 | 2.680 | 1.072 | 0.536 | 0.268 |
| Absorption value (A) | 1.160 | 0.538 | 0.198 | 0.093 | 0.046 |

DPPH standard curve was shown in FIG. 1, the linear equation of which was as follows: y=0.219x−0.0285; r=0.9994.

Preparation of DPPH Solution

DPPH was accurately weighed and placed in a 100 ml volumetric flask, and diluted to 100 ml with 95% ethanol to produce the DPPH solution.

Preparation of Test Drug Solution: the Test Drug was Accurately Weighed and Placed in a 100 ml volumetric flask, dissolved with 20 ml of 95% ethanol, adjusted to pH 7.5 and diluted to 100 ml with 95% ethanol.

Absorption Value Determination of Test Drug-DPPH Solution 5.0 ml of DPPH solution and 2.0 ml test drug solution were taken and placed in a 10 ml volumetric flask, fully shaken at room temperature for a certain time followed by determination of absorption value (A) at 517 nm.

Formula for calculating DPPH free radical scavenging ability of test drug, E (mgDPPH/mg):

$$E(\text{mgDPPH/mg}) = \frac{DPPH \text{ concentration (mg/100 ml)} \times 5/7 - (\text{absorption value } A + 0.0285)/0.219(\text{mg/100 ml})}{\text{Test drug concentration}}$$

$$C(\text{mg/100 ml}) \times 2/7$$

Formula for calculating DPPH free radical scavenging ability of test drug, V (mmolDPPH/mmol):

$$V(\text{mmolDPPH/mmol}) = \frac{E(\text{mgDPPH/mg})}{394.32/\text{test drug molecular weight}}$$

TABLE

Test results of scavenging DPPH free radical for 30 min

| Samples | Concentration of test drug C(mg/100 ml) | Absorption value of reaction liquid (A) | E(mgDPPH/mg) | | V(mmolDPPH/mmol) |
|---|---|---|---|---|---|
| DPPH | 5.080 | 0.760 | | | |
| Edaravone | 2.430 | 0.115 | 4.237 | 3.752 | 1.657 |
| | 1.215 | 0.397 | 4.785 | | |
| | 0.608 | 0.633 | 3.322 | | |
| | 0.304 | 0.699 | 3.195 | | |
| | 0.152 | 0.728 | 3.222 | | |
| Compound 1 | 2.440 | 0.486 | 1.792 | 1.687 | 0.856 |
| | 1.220 | 0.589 | 2.262 | | |
| | 0.610 | 0.712 | 1.252 | | |
| | 0.305 | 0.732 | 1.481 | | |
| | 0.153 | 0.744 | 1.650 | | |
| Compound 2 | 2.440 | 0.692 | 0.445 | 0.419 | 0.212 |
| | 1.220 | 0.717 | 0.561 | | |
| | 0.610 | 0.748 | 0.310 | | |
| | 0.305 | 0.753 | 0.368 | | |
| | 0.153 | 0.756 | 0.409 | | |
| Compound 3 | 2.540 | 0.052 | 4.464 | 3.510 | 1.942 |
| | 1.270 | 0.440 | 4.032 | | |
| | 0.635 | 0.650 | 2.770 | | |
| | 0.318 | 0.695 | 3.215 | | |
| | 0.159 | 0.729 | 3.067 | | |

TABLE 3

Determined values of reaction liquid absorption value at different times (DPPH: 5.080 mg/100 ml)

| Sample (concentration) | Reaction time (min) | | | | |
|---|---|---|---|---|---|
| | 30 | 60 | 90 | 120 | 150 |
| Compound 1 (0.61 mg/100 ml) | 0.712 | 0.701 | 0.678 | 0.654 | 0.641 |
| Compound 2 (0.61 mg/100 ml) | 0.748 | 0.735 | 0.720 | 0.705 | 0.693 |
| Compound 3 (0.64 mg/100 ml) | 0.650 | 0.648 | 0.646 | 0.647 | 0.645 |

In Table 2 and 3, Compound 1 was 2-methyl-benzo[d][1,3]oxazin[5-b]pyrazole-5-one, Compound 2 was 2-methyl-5-imino-benzo[d][1,3]oxazin[5-b]pyrazole (TR), and Compound 3 was 1-(2-cyanophenyl)-3-methylpyrazol-5-one.

Figure 2:
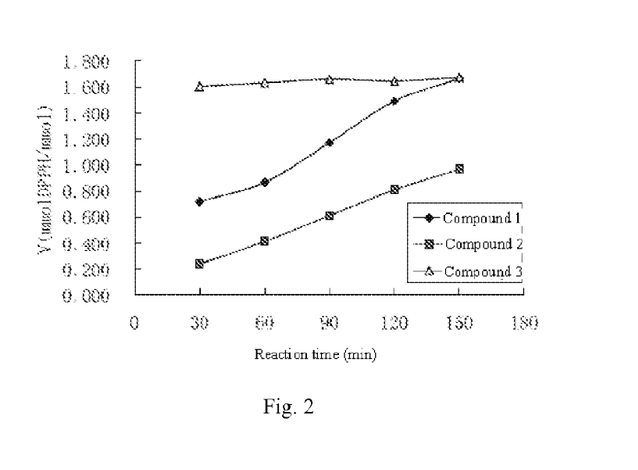
FIG. 2 is the relation graph of anti-DPPH free radical ability with reaction time.

The relationship of anti-DPPH free radical ability V (mmolDPPH/mmol) with reaction time (min) was shown in FIG. 2. The results of anti-DPPH free radical test showed that the DPPH free radical scavenging ability in 30 min of Compound 3 was the largest, and one molecular of Compound 3 could scavenge 1.942 molecular of DPPH free radical. One molecular of edaravone could scavenge 1.657 molecular of DPPH free radical, and the DPPH free radical scavenging ability of Compound 3 was slightly stronger than Edaravone. The DPPH free radical scavenging ability of Compound 1 and Compound 2 was related with the reaction time. With the reaction time, Compound 1 and Compound 2 were gradually hydrolyzed into Compound 3, and the DPPH free radical scavenging ability was gradually increased. The DPPH free radical scavenging ability of Compound 1 was one-eighth of Compound 3, and the DPPH free radical scavenging ability of Compound 1 at 150 min was equivalent with Compound 3.

Pharmacodynamic Experiments

Cerebral ischemia reperfusion model of middle cerebral artery occlusion (MCAO) was established in SD rats using the suture method of internal carotid artery. Test rats were administrated once 0.5 hours after ischemia reperfusion, then once every 2 hours, for totally three times. Neurological defect symptoms were observed 48 hours after cerebral ischemia. The animals were killed and specimens were taken to determine the cerebral infarction area and severity of brain injury. 2-methyl-5-imino-benzo[d][1,3]oxazin[5-b]pyrazole (hereinafter referred to as TR) was used as test substance, and nimodipine was used for reference.

Influence of TR on Neurological Defect Symptoms

Figure 3:
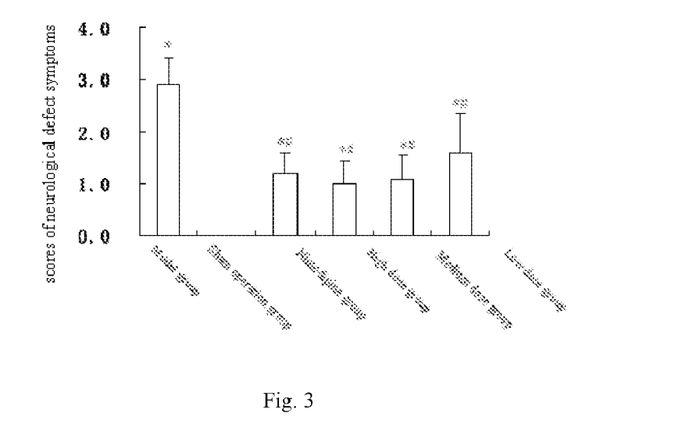
FIG. 3 is the impact column drawing of TR on neurological defect symptoms, wherein the results are illustrated as X±SD, compared with the sham operation group, *P<0.05, and compared with the model group, #P<0.05.

The severity scores of neurological defect symptoms were shown in Table 4 and FIG. 3. There was significant difference between the model group and the sham operation group (F5, 41=28.05, P<0.001), which showed that cerebral ischemia-reperfusion can cause serious neurological defect symptoms. Compared with the model group, the neurological defect symptoms were significantly reduced in the TR high dose group (F5, 41=28.05, P<0.001), the medium dose group (F5, 41=28.05, P<0.001), the low dose group (F5, 41=28.05, P=0.001), and the nimodipine group (F5, 41=28.05, P<0.001).

TABLE 4

Influence of TR on neurological defect symptoms

| Group | Total number | Operation failed | Death | n | Dose (mg/kg) | Scores of neurological defect symptoms |
|---|---|---|---|---|---|---|
| Model group | 12 | 3 | 2 | 7 | | 2.9 ± 0.53* |
| Sham operation group | 7 | 0 | 0 | 7 | | 0.0 ± 0.00 |
| Nimodipine group | 12 | 0 | 2 | 10 | 0.4 | 1.2 ± 0.41*# |
| TR6.0 mg/kg group | 11 | 2 | 1 | 8 | 6.0 | 1.0 ± 0.46*# |
| TR3.0 mg/kg group | 11 | 3 | 0 | 8 | 3.0 | 1.1 ± 0.44*# |
| TR1.5 mg/kg group | 12 | 2 | 3 | 7 | 1.5 | 1.6 ± 0.75* |

X ± SD, compared with Sham operation group,
*P < 0.05; and compared with model group,
P < 0.05.

Influence of TR on Cerebral Infarction Area

Figure 4:
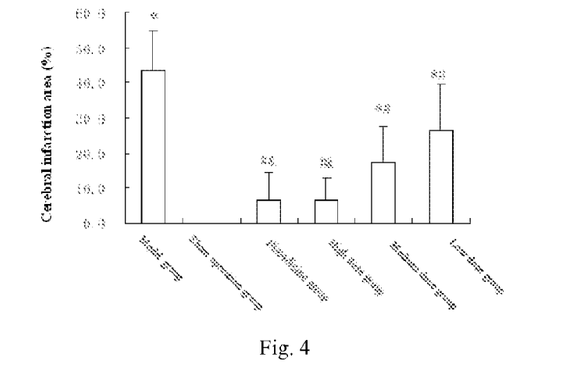
FIG. 4 is the impact of TR on cerebral infarction area, wherein the results are illustrated as X±SD, compared with the sham operation group, *P<0.05, compared with the model group, #P<0.05, and compared with the low dose group, &P<0.05.

The cerebral infarction area result of each group was shown in Table 5 and FIG. 4. There was significant difference between the model group and the sham operation group (F5, 41=23.34, P<0.001), which showed that cerebral ischemia-reperfusion can cause significant cerebral infarction. Compared with the model group, the cerebral infarction area was significantly reduced in the TR high dose group (F5, 41=23.34, P<0.001), the medium dose group (F5, 41=23.34, P<0.001), the low dose group (F5, 41=23.34, P=0.044), and the nimodipine group (F5, 41=23.34, P<0.001). There was significant difference between the TR high dose group and the TR low dose group (F5, 41=23.34, P=0.009).

TABLE 5

Influence of TR on cerebral infarction area

| Group | Total number | Operation failed | Death | n | Dose (mg/kg) | Cerebral infarction area (%) |
|---|---|---|---|---|---|---|
| Model group | 12 | 3 | 2 | 7 | | 43.7 ± 11.29* |
| Sham operation group | 7 | 0 | 0 | 7 | | 0.0 ± 0.00 |
| Nimodipine group | 12 | 0 | 2 | 10 | 0.4 | 6.7 ± 6.30[#&] |
| TR6.0 mg/kg group | 11 | 2 | 1 | 8 | 6.0 | 6.7 ± 6.30[#&] |
| TR3.0 mg/kg group | 11 | 3 | 0 | 8 | 3.0 | 17.4 ± 10.05*[#] |
| TR1.5 mg/kg group | 12 | 2 | 3 | 7 | 1.5 | 26.5 ± 13.24* |

X ± SD, compared with Sham operation group,
*P < 0.05; compared with model group,
[#]P < 0.05, and compared with the low dose group,
[&]P < 0.05.

Influence of TR on Brain Injury

Figure 5:
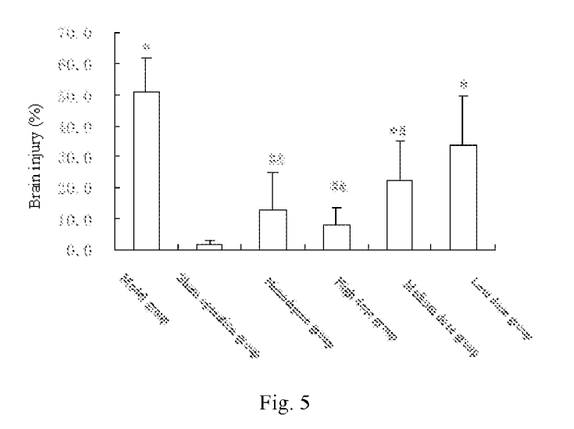
FIG. 5 is the impact column drawing of TR on cerebral infarction area, wherein the results are illustrated as X±SD, compared with the sham operation group, *P<0.05, compared with the model group, #P<0.05, and compared with the low dose group, &P<0.05.
Figure 6:
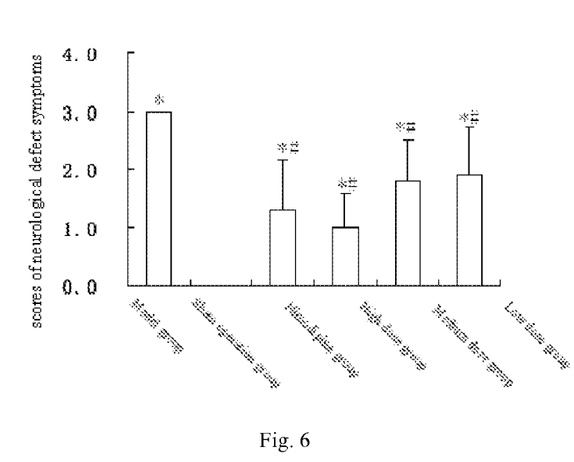
FIG. 6 is the impact column drawing of TR on cerebral infarction area, wherein the results are illustrated as X±SD, compared with the sham operation group, *P<0.05, compared with the model group, #P<0.05, and compared with the low dose group, &P<0.05.

The brain injury result of each group was shown in Table 6 and FIG. 5. There was significant difference between the model group and the sham operation group (F5, 41=20.52, P<0.001), which showed that cerebral ischemia-reperfusion can cause significant brain injury. Compared with the model group, the brain injury was significantly reduced in the TR high dose group (F5, 41=20.52, P<0.001), the medium dose group (F5, 41=20.52, P=0.001), and the nimodipine group (F5, 41=20.52, P<0.001). There was significant difference between the TR high dose group and the TR low dose group (F5, 41=20.52, P=0.004).

TABLE 6

Influence of TR on brain injury

| Group | Total number | Operation failed | Death | n | Dose (mg/kg) | Cerebral infarction area (%) |
|---|---|---|---|---|---|---|
| Model group | 12 | 3 | 2 | 7 | | 51.1 ± 10.70* |
| Sham operation group | 7 | 0 | 0 | 7 | | 1.8 ± 1.57 |
| Nimodipine group | 12 | 0 | 2 | 10 | 0.4 | 12.8 ± 12.09[#&] |
| TR6.0 mg/kg group | 11 | 2 | 1 | 8 | 6.0 | 8.1 ± 5.68[#&] |
| TR3.0 mg/kg group | 11 | 3 | 0 | 8 | 3.0 | 22.7 ± 12.10*[#] |
| TR1.5 mg/kg group | 12 | 2 | 3 | 7 | 1.5 | 33.6 ± 16.08* |

X ± SD, compared with Sham operation group,
*P < 0.05; compared with model group,
[#]P < 0.05, and compared with the low dose group,
[&]P < 0.05.

Influence of TR on Neurological Defect Symptoms

Figure 1:
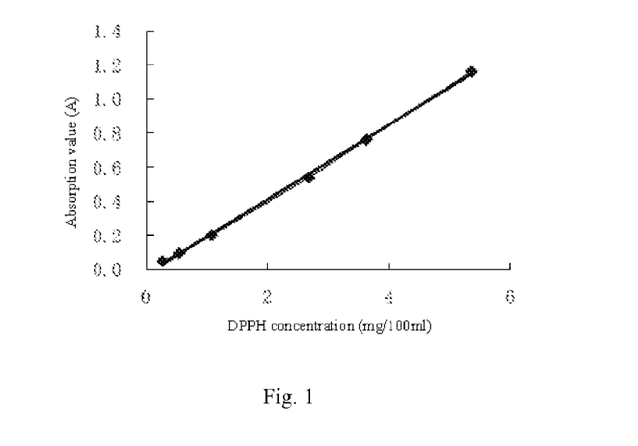
FIG. 1 is DPPH standard curve.

The severity scores of neurological defect symptoms were shown in Table 1 and FIG. 1. There was significant difference between the model group and the sham operation group (F5, 41=28.05, P<0.001), which showed that cerebral ischemia-reperfusion can cause serious neurological defect symptoms. Compared with the model group, the neurological defect symptoms were significantly relieved in the TR high dose group (F5, 41=28.05, P<0.001), the medium dose group (F5, 41=28.05, P<0.001), the low dose group (F5, 41=28.05, P=0.001), and the nimodipine group (F5, 41=28.05, P<0.001). The results illustrated that TR can improve the neurological defect symptoms of cerebral ischemia-reperfusion animals.

TABLE 7

Influence of TR on neurological defect symptoms

| Group | Total number | Operation failed | Death | n | Dose (mg/kg) | Scores of neurological defect symptoms |
|---|---|---|---|---|---|---|
| Model group | 11 | 1 | 1 | 9 | — | 3.0 ± 0.00* |
| Sham operation group | 9 | 0 | 0 | 9 | — | 0.0 ± 0.00 |
| Nimodipine group | 10 | 3 | 07 | 7 | 0.4 | 1.3 ± 0.86*[#] |
| TR6.0 mg/kg group | 11 | 1 | 1 | 9 | 6.0 | 1.0 ± 0.58*[#] |
| TR3.0 mg/kg group | 11 | 3 | 0 | 8 | 3.0 | 1.8 ± 0.70*[#] |
| TR1.5 mg/kg group | 10 | 3 | 0 | 7 | 1.5 | 1.9 ± 0.84*[#] |

X ± SD, compared with Sham operation group,
*P < 0.05 and compared with model group,
[#]P < 0.05.

Influence of TR on Water Content in Brain

Figure 7:
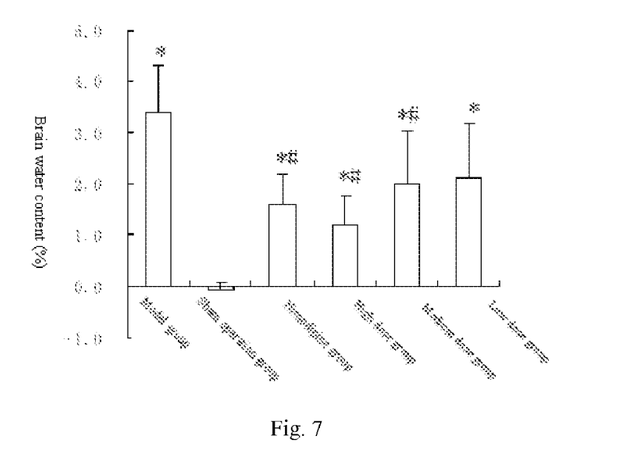
FIG. 7 is the impact column drawing of TR on brain water content, wherein the results are illustrated as X±SD, compared with the sham operation group, *P<0.05, and compared with the model group, #P<0.05.

The brain water content of each group was shown in Table 8 and FIG. 7. There was significant difference between the model group and the sham operation group (F5, 42=20.06, P<0.001), which showed that cerebral ischemia-reperfusion can cause brain edema. Compared with the model group, the water content in brain was significantly reduced in the TR high dose group (F5, 42=20.06, P<0.001), the medium dose group (F5, 42=20.06, P=0.039), and the nimodipine group (F5, 42=20.06, P=0.003). No obvious difference was found in the low dose group and the model group (F5, 42=20.06, P=0.086).

TABLE 8

Influence of TR on water content in brain

| Group | Total number | Operation failed | Death | n | Dose (mg/kg) | Variation value of water content in brain (%) |
|---|---|---|---|---|---|---|
| Model group | 11 | 1 | 1 | 9 | — | 3.4 ± 0.90* |
| Sham operation group | 9 | 0 | 0 | 9 | — | −0.1 ± 0.18 |
| Nimodipine group | 10 | 3 | 7 | 7 | 0.4 | 1.6 ± 0.59*# |
| TR6.0 mg/kg group | 11 | 1 | 1 | 9 | 6.0 | 1.2 ± 0.55*# |
| TR3.0 mg/kg group | 11 | 3 | 0 | 8 | 3.0 | 2.0 ± 1.01*# |
| TR1.5 mg/kg group | 10 | 3 | 0 | 7 | 1.5 | 2.1 ± 1.08* |

X ± SD, compared with Sham operation group,
*P < 0.05 and compared with model group,
P < 0.05.

Influence of TR on SOD Activity and MDA Level in Damaged Brain Tissue

Figure 8:
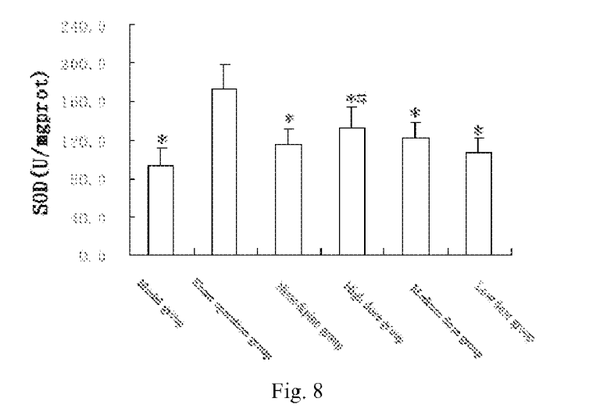
FIG. 8 is the impact column drawing of TR on brain tissue SOD (U/mgprot) activity, wherein the results are illustrated as X±SD, compared with the sham operation group, *P<0.05, and compared with the model group, #P<0.05.
Figure 9:
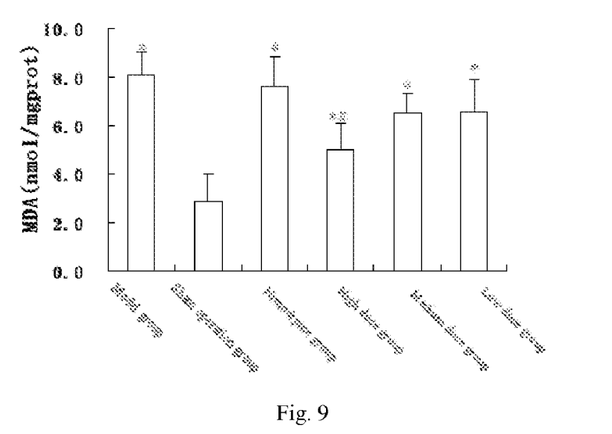
FIG. 9 is the impact column drawing of TR on brain tissue MDA (nmol/mgprot) activity, wherein the results are illustrated as X±SD, compared with the sham operation group, *P<0.05, and compared with the model group, #P<0.05.

The brain tissue SOD activity and MDA level of each group was shown in Table 9 and FIGS. 8 and 9. There was significant difference between the model group and the sham operation group (F5, 42=26.96, P<0.001), MDA content was significantly increased (F5, 42=26.96, P<0.001) and SOD activity was obviously reduced (F5, 42=17.13, P<0.001), which showed that cerebral ischemia-reperfusion can cause lipid peroxidation of injured brain tissue. Compared with the model group, the MDA content was significantly decreased in the TR high dose group (F5, 42=26.96, P<0.001). No obvious difference was found in the TR medium dose group (F5, 42=26.96, P=0.141), the low dose group (F5, 42=26.96, P=0.211), the nimodipine group (F5, 42=26.96, P=0.961) and the model group. Compared with the model group, the SOD activity was significantly increased in the TR high dose group (F5, 42=17.13, P=0.007). No obvious difference was found in the TR medium dose group (F5, 42=17.13, P=0.157), the low dose group (F5, 42=17.13, P=0.826), the nimodipine group (F5, 42=17.13, P=0.435) and the model group.

TABLE 9

Influence of TR on brain tissue SOD activity (U/mgprot) and MDA content (nmol/mgprot)

| Group | Total number | Operation failed | Death | n | Dose (mg/kg) | SOD (U/mgprot) | MDA (nmol/mgprot) |
|---|---|---|---|---|---|---|---|
| Model group | 11 | 1 | 1 | 9 | — | 92.5 ± 18.3* | 8.1 ± 0.91* |
| Sham operation group | 9 | 0 | 0 | 9 | — | 172.9 ± 26.4 | 2.9 ± 1.10 |
| Nimodipine group | 10 | 3 | 07 | 7 | 0.4 | 114.8 ± 16.4* | 7.6 ± 1.28* |
| TR6.0 mg/kg group | 11 | 1 | 1 | 9 | 6.0 | 132.7 ± 21.0*# | 5.0 ± 1.10*# |
| TR3.0 mg/kg group | 11 | 3 | 0 | 8 | 3.0 | 121.6 ± 16.8* | 6.5 ± 0.81* |
| TR1.5 mg/kg group | 10 | 3 | 0 | 7 | 1.5 | 107.1 ± 15.5* | 6.6 ± 1.30* |

X ± SD, compared with Sham operation group,
*P < 0.05 and compared with model group,
P < 0.05.

The reperfusion model results of SD rats with middle cerebral artery occlusion showed that TR can significantly improve the neurological defect symptoms of cerebral ischemia-reperfusion animals in a dose dependent manner, decreased the brain infarction area, reduced the brain damage, relieved the cerebral edema, inhibit the lipid peroxidation of injured brain tissue with onset dose of 3 mg/kg.

What is claimed is:

1. A compound of formula (II), 2-methyl-5-imino-benzo[d][1,3]oxazin[5-b]pyrazole, or a pharmaceutically acceptable salt thereof.

2. A method for preparing the compound of formula II of claim 1, comprising steps of (1) reacting compound M with an acetyl acetate in the existence of a base to give compound N; and (2) making compound N ring-closed in hydrogen chloride gas:

-continued formula II

3. The method according to claim 2, wherein said step (1) being conducted in a solvent selected from ethanol or methanol at a temperature from 40 to 80° C., and said base being selected from sodium methoxide and sodium ethoxide.

4. The method according to claim 2, wherein said step (2) being conducted in a solvent selected from dichloromethane and THF at a temperature from 20 to 40° C.

5. A pharmaceutical composition comprising the compound or pharmaceutically acceptable salts thereof according to claim 1 in an amount of therapeutical effect and a pharmaceutically acceptable excipient.

\* \* \* \* \*